(12) United States Patent
Tanabe

(10) Patent No.: US 7,856,086 B2
(45) Date of Patent: Dec. 21, 2010

(54) X-RAY GENERATOR

(75) Inventor: Eiji Tanabe, Kanagawa (JP)

(73) Assignee: AET, Inc., Kawasaki (JP)

( * ) Notice: Subject to any disclaimer, the term of this patent is extended or adjusted under 35 U.S.C. 154(b) by 84 days.

(21) Appl. No.: 12/332,100

(22) Filed: Dec. 10, 2008

(65) Prior Publication Data

US 2009/0154650 A1    Jun. 18, 2009

(30) Foreign Application Priority Data

Dec. 13, 2007  (JP) .............................. 2007-322483

(51) Int. Cl.
*H01J 35/30* (2006.01)
*H01J 35/14* (2006.01)
(52) U.S. Cl. ...................... 378/137; 378/138
(58) Field of Classification Search ............... 378/137, 378/138, 119, 121, 143
See application file for complete search history.

(56) References Cited

U.S. PATENT DOCUMENTS

| 4,521,901 | A  | * | 6/1985  | Rand ........................... 378/138 |
| 5,663,999 | A  |   | 9/1997  | Siochi |
| 6,330,300 | B1 |   | 12/2001 | Siochi |
| 7,140,771 | B2 | * | 11/2006 | Leek ........................... 378/203 |
| 7,486,775 | B2 | * | 2/2009  | Forster et al. ................ 378/137 |
| 7,634,062 | B2 | * | 12/2009 | Tanaka et al. ................ 378/137 |
| 2006/0106301 | A1 | * | 5/2006 | Kats ........................... 600/415 |
| 2008/0198970 | A1 | * | 8/2008 | Kirshner et al. ............. 378/137 |
| 2009/0232279 | A1 | * | 9/2009 | Lesiak et al. ................ 378/138 |

FOREIGN PATENT DOCUMENTS

| JP | 9-239044    | 9/1997 |
| JP | 10-71214    | 3/1998 |
| JP | 2001-070466 | 3/2001 |
| JP | 2002-153567 | 5/2002 |

\* cited by examiner

*Primary Examiner*—Edward J Glick
*Assistant Examiner*—Anastasia Midkiff
(74) *Attorney, Agent, or Firm*—Orion Consulting, Ltd.; Joseph P. Farrar

(57) ABSTRACT

An electron beam corresponding to radiation intensity data is output from an electron source by supplying high energy pulses p-1 through p-n, which correspond to the radiation intensity data of a radiation field, to the electron source from a power source 108. This electron beam is deflected so as to be incident in parallel to the medial axis of a plurality of X-ray target tubes 104-1 through 104-n by a deflection means comprising electromagnets, such that X-ray beams x-1 through x-n, which are produced when the electron beam collides with an inner wall of an X-ray target tube are irradiated with a desired intensity.

14 Claims, 12 Drawing Sheets

X-RAY GENERATOR

BACKGROUND OF THE INVENTION

1. Field of the Invention

The present invention concerns an X-ray generator radiating an X-ray beam in which the radiation intensity is modulated. In particular, it relates to an X-ray generator that can form a new radiation field by bundling a plurality of X-ray tubes so that the radiation field of the X-ray beam, which is formed by a plurality of individual X-ray beams from the plurality of X-ray tubes, is narrow and wherein the radiation intensity for each of the individual X-ray beams can be set individually. Even more particularly, the present invention relates to an X-ray generator which is suitable for use in an X-ray therapeutic apparatus, said X-ray therapeutic apparatus comprising one or more of the X-ray generators.

2. Description of the Related Art

Intensity modulated radiation therapy (hereinafter abbreviated to IMRT) can reduce a radiation dose to normal tissues around the lesion portion by changing such factors as a radiation angular degree, a radiation field, and a radiation intensity of radioactive rays according to a shape of the lesion portion, so that the radioactive rays concentrate on the lesion portion. The apparatus for IMRT which modulates intensity using a multi-leaf collimator placed between a radiation aperture and a patient is known (for example, as illustrated to Japanese Unexamined Patent Application Publication No. H09-239044, Japanese Unexamined Patent Application Publication No. H10-071214, Japanese Unexamined Patent Application Publication No. 2002-153567, and Japanese Unexamined Patent Application Publication No. 2001-070466).

A therapeutic apparatus as claimed in Japanese Unexamined Patent Application Publication No. H09-239044, as shown in FIG. 15, comprises a multi-leaf collimator 13 controlled by a gantry 11 and a multi-leaf collimator control unit 12. The therapeutic apparatus can obtain a dose distribution corresponding to the three-dimensional shape of the tumor of the patient by irradiating the patient with radiation beams while changing a shape of the radiation field of the multi-leaf collimator 13 in accordance with the rotation angle of the gantry 11.

A method of obtaining the dose distribution such that the intensity of the radiation beams changes optimally is described in Japanese Unexamined Patent Application Publication No. H10-071214. The method divides a three-dimensional intensity map of the radiation field into multiple sections of intensity, and makes an intensity map of the radiation beam for every section. The intensity map is sliced to a matrix showing whether the radiation is required or not. The shape of the aperture of the collimator is set according to the matrix. Afterward, an object is irradiated with X-rays. This radiation apparatus obtains the optimum dose distribution by repeating this process.

A method of obtaining the dose distribution increasing the resolution of the radiation dose at the boundaries of a treatment area is described in Japanese Unexamined Patent Application Publication No. 2002-153567. The method divides the treatment area into a plurality of cells having a predetermined treatment intensity level. For those cells including critical tissues at the boundaries of the treatment area, the leaf of the multi-leaf collimator is moved to a position at an edge margin which sets a position in the middle of the cell and not at the edge of the cell, while radioactive rays are radiated.

A method of irradiating an object with radioactive rays described in Japanese Unexamined Patent Application Publication No. 2001-070466 resolves further a two-dimensional radiation intensity distribution quantized by levels of predetermined positive integers into a plurality of two-dimensional radiation intensity distributions of relative intensity 1. In each two-dimensional radioactive ray distribution generated by such resolving, there are only shielded object cells and radiation object cells, and the radiation intensity to a radiation object cell is the same (relative intensity 1). After this, the multi-leaf collimator is placed according to the generated two-dimensional radioactive ray distribution, and the radiation rays are radiated.

However, each invention described in Japanese Unexamined Patent Application Publication No. H09-239044, Japanese Unexamined Patent Application Publication No. H10-071214, Japanese Unexamined Patent Application Publication No. 2002-153567 and Japanese Unexamined Patent Application Publication No. 2001-070466 describes a method of obtaining cumulatively the intensity distribution of the required radiation dose by repeating the irradiation while changing the shape of the aperture of the multi-leaf collimator. According to the invention of Japanese Unexamined Patent Application Publication No. H09-239044, a dose distribution of modulated radiation intensity in three-dimensional space can be obtained by rotation of the gantry. However, as the two-dimensional plane radiation intensity is the same, intensity modulation in the two-dimensional plane cannot be obtained. Therefore, the accuracy of dose distribution obtained in the three-dimensional space is not sufficient.

The invention described in Japanese Unexamined Patent Application Publication No. H10-071214, Japanese Unexamined Patent Application Publication No. 2002-153567 and Japanese Unexamined Patent Application Publication No. 2001-070466 can obtain an intensity modulation in the two-dimensional plane by multiple irradiation, but the irradiation has to be performed at least as many times as the intensity level requires. When there is a plurality of shielded areas in the direction in which the leaf moves, even if there is only one intensity level, the leaf has to be moved and the irradiation performed multiple times.

In late years, with improvements in imaging diagnostic technology such as CT scanner, a three-dimensional shape of the lesion portion can be grasped in detail. With this, it becomes required to raise an accuracy of the radiation therapy adapting for a symptom of each part of the lesion portion. However, when an accuracy of the radiation therapy is going to be raised by using the multi-leaf collimator, a radiation number of times will be increased, burdens of the patient increase to need time for a treatment. Even more particularly, if a treatment time becomes long, there is a limit in the conventional method of improving treatment accuracy by increasing a radiation number of times because it becomes difficult to fix a lesion portion.

It is necessary to irradiate with a rotational transfer of the gantry to get a dose distribution corresponding to the three-dimensional shape of the lesion portion in the invention described in Japanese Unexamined Patent Application Publication No. H09-239044, Japanese Unexamined Patent Application Publication No. H10-071214, Japanese Unexamined Patent Application Publication No. 2002-153567 and Japanese Unexamined Patent Application Publication No. 2001-070466. However, because the gantry is heavy, the backlashes and arcuations occur easily while the gantry rotates. As shown in Japanese Unexamined Patent Application Publication No. 2002-153567, when the resolution higher than ⅓ cm is required, the three-dimensional radiation of radioactive rays after a gantry rotational transferred has a problem in respect of accuracy.

Also, because the leaf of the multi-leaf collimator is rectangular, when the treatment area has unevenness, it is difficult to position the leaf along the bound of the treatment area. Even more particularly, there is a problem to injure normal tissues of the bound vicinity because a leaf malfunctions in the location with a rippling dose distribution in the bound part of the radiation area.

It is an object of the present invention to provide the X-ray generator which can obtain immediately a two-dimensional dose distribution which the intensity is finely modulated corresponding to the desired radiation dose for X-ray therapy to each part of the lesion portion by solving previously described problems. Even more particularly, it is an object of the present invention to provide the X-ray generator which is suitable for X-ray generator in the X-ray therapeutic apparatus.

SUMMARY OF THE INVENTION

The X-ray generator comprises a power source outputting high energy pulses, an electron source radiating high energy electron beams from the high energy pulses, a microwave source supplying a high power microwave to the electron source, an X-ray source comprising a bundle of a plurality of X-ray tubes radiating X-rays by a collision of the high-energy electron beams, arranged to continue the radiation fields of the X-ray tubes, a deflection means deflecting the direction of the high energy electron beams so that the high energy electron beams are incident in parallel to the medial axis of the X-ray tubes, and are incident on the X-ray tubes sequentially, a data setting unit that sets the radiation intensity of the X-ray tubes so that the predetermined dose distribution is obtained in the field of the X-ray tubes, and a control means setting the high energy pulse width according to the radiation intensity data, synchronizing a timing to output the high energy pulse and a timing to radiate the electron beams and a timing to excite the deflection means.

The deflection means comprises a first deflection electromagnet deflecting the high energy electron beam to an inlet aperture of any one of the plurality of X-ray tubes and a second deflection electromagnet deflecting the high energy electron beams deflected by the first deflection electromagnet so that the high energy electron beams are incident in parallel to the medial axis of the X-ray tubes.

The X-ray source comprises the X-ray tubes arranged in a line, and wherein the high energy electron beams are sequentially irradiated from one end of the X-rays tubes to the other opposite end.

The deflection means comprises a deflection electromagnet deflecting the high energy electron beam to an inlet aperture of any X-ray tubes and the X-ray tube arranging radially so that the direction of the high energy electron beams deflected by the deflection electromagnet are in parallel to the medial axis of the X-ray tubes. The deflection means comprises a quadrupole electromagnet.

The X-ray tube comprises a truncated cone shape having a smaller diameter of an outlet aperture than an inlet aperture, and wherein the inner wall of the X-ray tube acts as an X-ray target tube radiating X-ray beams by the collision of high energy electron beams with the inner wall of the X-ray tube.

The X-ray source comprises the X-ray tubes arranged so that radiation fields of ½ width for the maximum radiation intensity are adjacent in succession.

The X-ray generator of the present invention may be applied to an X-ray therapeutic apparatus, with one or more of the X-ray generators being installed in different positions of the three-dimensional space including the treatment couch, and wherein X-rays are radiated intensively on the lesion portion of a patient fixed on the treatment couch in the space.

The X-ray generator of the present invention, applied to an X-ray therapeutic apparatus comprises translation means to move the treatment couch in parallel perpendicularly to the X-ray generator and control means which control by synchronizing the X-ray generator and the translation means.

The X-ray generator of the present invention may be applied to the X-ray therapeutic apparatus able to vary a relative position of the lesion portion of a patient fixed on a treatment couch and wherein the X-ray generator is installed in the X-ray head, so as to radiating X-rays to the lesion portion of the patient.

According to the X-ray generator of the present invention, it can provide immediately desired two-dimensional dose distribution by subdividing the radiation dose needed for each part of the lesion portion without using a multi-leaf collimator. More particularly, the present invention can provide an X-ray therapeutic apparatus that is able to treat effectively a lesion portion with reduced burden on a patient by shortening treatment time and holding down radiation dosage to normal cells.

The preferred embodiments of the X-ray generator and X-ray therapeutic apparatus with the X-ray generators will be described with reference to the accompanying drawings in detail as follows.

DESCRIPTION OF THE PREFERRED EMBODIMENTS

Detailed Description of a Preferred First Embodiment

Figure 1:
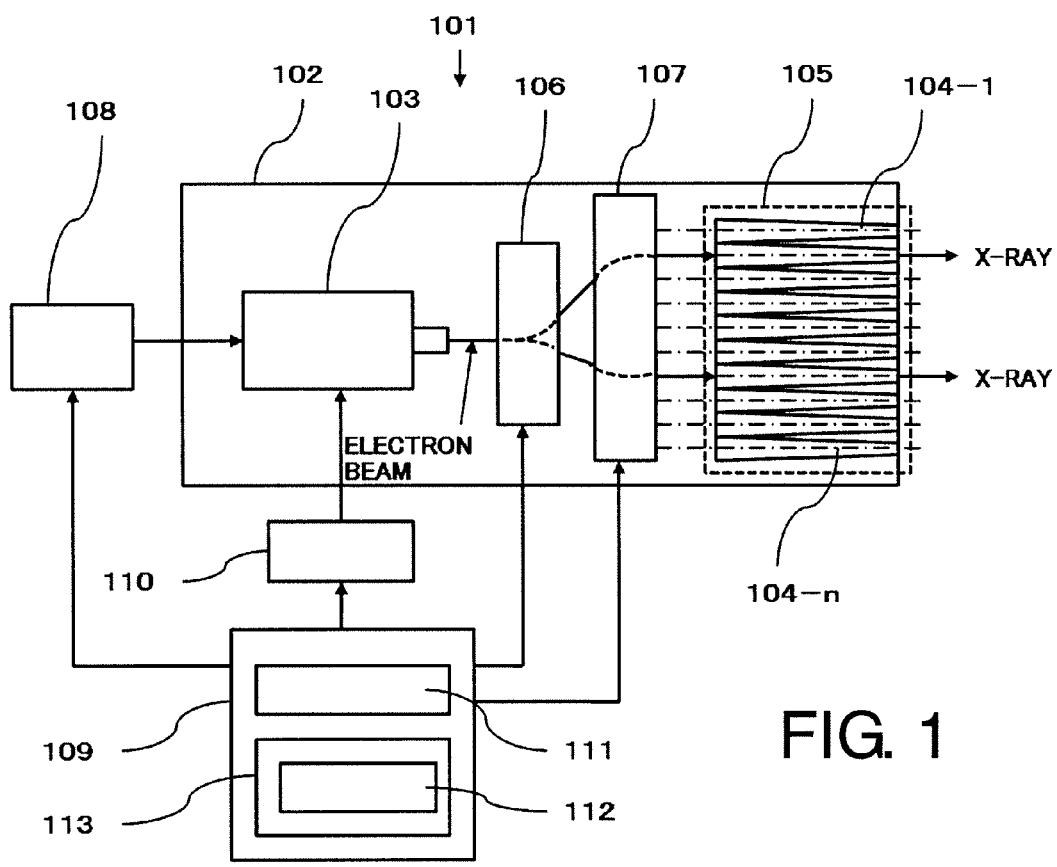
FIG. 1 is a block diagram of the X-ray generator according to a preferred first embodiment of the present invention.

FIG. 1 shows a schematic representation of a configuration of an X-ray generator according to a preferred first embodiment of the present invention. In FIG. 1, an X-ray generator 101 comprises an electron source (hereinafter referred to as an electron gun) 103 radiating high energy electron beams to a vacuum chamber 102, an X-ray target tube array 105 comprising a plurality of X-ray target tubes 104-1 through 104-n arranged in a line which radiates X-ray beam by colliding the high energy electron beams radiated by the electron gun 103, and a first deflection electromagnet 106 and a second deflection electromagnet 107 that deflect the high energy electron beams which are radiated by the electron gun 103. Outside the vacuum chamber 102 are provided a power source 108 outputs the high energy pulse to the electron gun 103 with a predetermined timing, a microwave source 110 supplies the high voltage microwave to the electron gun 103, and a controller 109 controls the power source 108, the microwave source 110, the first deflection electromagnet 106 and the second deflection electromagnet 107.

A radiation control program 111 and treatment field radiation intensity data 113 which comprises radiation field radiation intensity data 112 of the X-ray target tube array 105 are stored in the controller 109. The radiation field radiation intensity data 112 presents a radiation dose of each X-ray target tubes 104-1 through 104-n comprising the X-ray target tube array 105. The radiation control program 111 controls the high voltage microwave source 110, the excitation of the first deflection electromagnet 106 and the second deflection electromagnet 107, and the width of the high energy pulse output from the power source 108 so that high energy electron beams which are radiated from the electron gun 103 reflect in turn on the X-ray target tubes 104-1 through 104-n arranged in a line.

Figure 2:
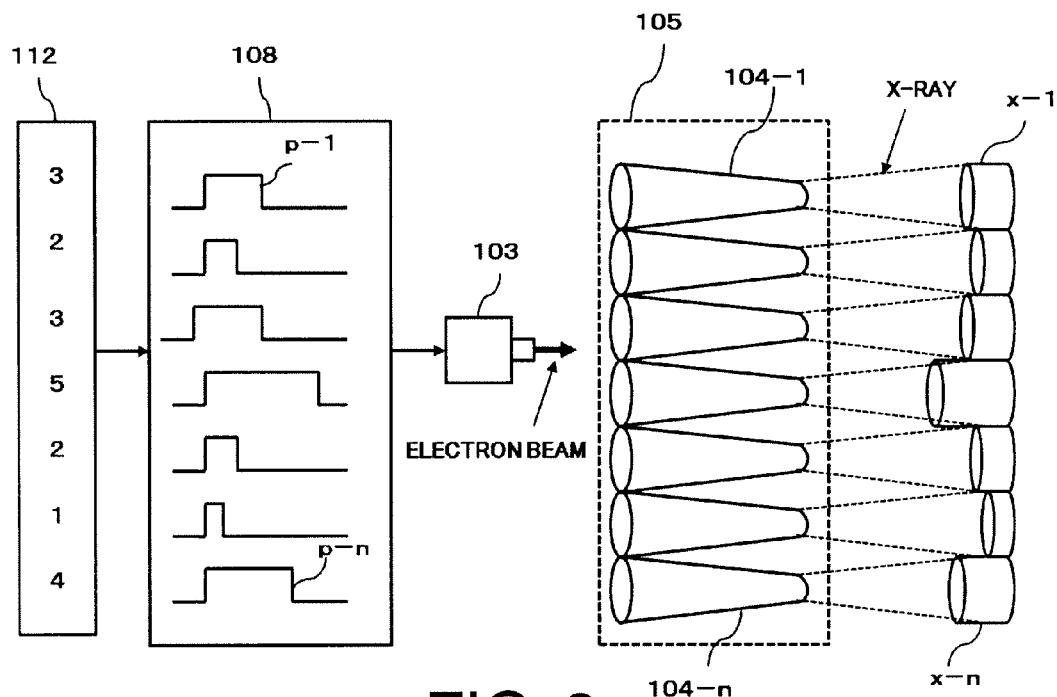
FIG. 2 is a diagram describing the state to modulate the intensity of the radiation field of the X-ray target tube array in accordance with the radiation intensity data of the radiation field concerning the preferred first embodiment of the present invention.

FIG. 2 shows a state of modulated intensity of the radiation field of the X-ray target tube array in accordance with the radiation intensity data of the radiation field according to the preferred first embodiment of the present invention. In FIG. 2, when the high energy pulses p-1 through p-n corresponding to the desired radiation dose are output from the power source 108, the electron beams corresponding to the high energy pulses p-1 through p-n are radiated in turn from the electron gun 103. The X-ray beams x-1 through x-n are radiated by the electron beams colliding with the inner walls of the X-ray target tubes 104-1 through 104-n comprising the X-ray target tube array 105. The intensity of the X-ray beams x-1 through x-n is modulated according to the radiation field radiation intensity data 112.

The first deflection electromagnet 106 and the second deflection electromagnet 107 shown in FIG. 1 are parallel planar electromagnets, respectively. The first deflection electromagnet 106 acts to bend the high energy electron beams in the direction of a desired target tube in the X-ray target tube array 105. The second deflection electromagnet 107 deflects the high energy electron beams bent by the first deflection electromagnet in parallel to the medial axis of the desired X-ray target tube.

Figure 3:
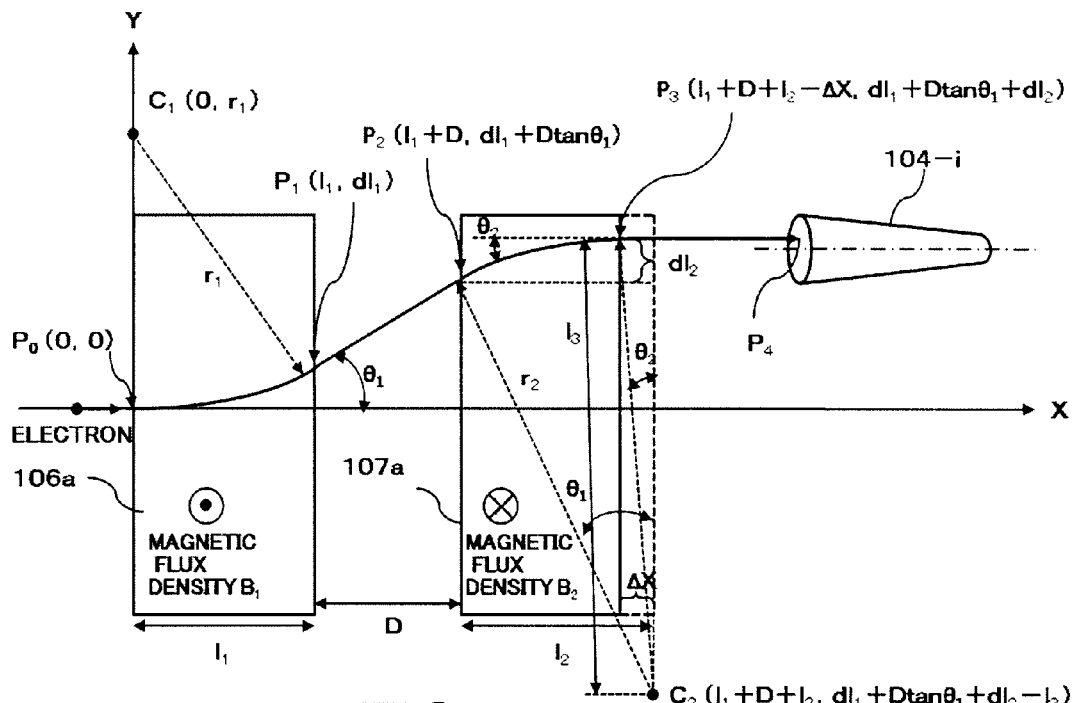
FIG. 3 is a diagram describing the deflection of the electron beam by the deflection electromagnet according to the preferred first embodiment of the present invention.

FIG. 3 shows the deflected state of the high energy electron beams. In FIG. 3, a rectangular area 106a shows the magnetic field of the magnetic flux density $B_1$ generated by the first deflection electromagnet 106, and a rectangular area 107a shows the magnetic field of the magnetic flux density $B_2$ generated by the second deflection electromagnet 107. The direction of the magnetic field 106a is set to a positive direction (the direction which is from back to front of the plane of the sheet of paper on which FIG. 3 is drawn) of a Z-axis perpendicular to an X-Y plane, and the direction of the magnetic field 107a is set to the opposite direction (the direction which is from front to back).

In FIG. 3, when the electron radiated from the electron gun 103 penetrates at a velocity v at a point $P_0$ (0,0) of the magnetic field of this magnetic flux density $B_1$, a Lorentz force shown in expression (1) acts on the electron.

$$F = e[(v \times B_1)] \tag{1}$$

The direction of the force is the positive direction of the Y-axis. The force acts in a direction parallel to the X-Y plane without a Z component. The electron moves uniformly in a circular orbit of radius $r_1$ because this Lorentz force and the centrifugal force with the electron velocity are in balance. In other words, the motion equation is presented in (2).

$$\frac{mv^2}{r_1} = evB_1 \tag{2}$$

Here, m is the mass of a moving electron, v is the speed of an electron, and e is the electric charge of an electron. The coordinate of the point which the electron crosses the edge of the magnetic field 106a is $P_1$ ($l_1$, $dl_1$). In other words, the electron is biased a distance $dl_1$ in the Y-axis direction by the magnetic field 106a. The electron moves over a circumference expressed in the next equation.

$$x^2 + (y - r_1)^2 = r_1^2$$

Therefore, the next equation is formed.

$$l_1^2 + (dl_1 - r_1)^2 = r_1^2 \tag{3}$$

Thus, $$dl_1 = r_1 \left(1 - \sqrt{1 - \left(\frac{l_1}{r_1}\right)^2}\right) \tag{4}$$

But, the next condition is kept.

$$l_1 \leq r_1$$

Because the electron velocity is almost equal to the velocity of light, special relativity applies and the next equation is provided from equation (2).

$$r_1 = \frac{mv}{eB_1} = \frac{m_0}{\sqrt{1-\left(\frac{v}{c}\right)^2}} \times \frac{v}{eB_1} = \frac{m_0 v}{e \times \sqrt{1-\left(\frac{v}{c}\right)^2}} \times \frac{1}{B_1} \quad (5)$$

Here, $m_0$ presents the rest mass of an electron and c presents the velocity of light. Also, the electron velocity v accelerated in the voltage V is given by the following equation.

$$\frac{v}{c} = \sqrt{1 - \frac{1}{\left(1 + \frac{eV}{m_0 c^2}\right)^2}} \quad (6)$$

Because the deflection angle $\theta_1$ of the direction of movement an electron to the X-axis at the point $P_1$ is the tangent of the point $P_1$ of the quadratic curve $x^2 + (y-r_1)^2 = r_1^2$, $\theta_1$ is expressed as follows.

$$\frac{dy}{dx_{P_1(l_1,dl_1)}} = \tan\theta_1 = \left(-\frac{x}{y-r_1}\right)_{P_1(l_1,dl_1)} = \frac{l_1}{r_1 - dl_1} \quad (7)$$

$$\theta_1 = \tan^{-1}\left(\frac{l_1}{r_1 - dl_1}\right) \quad (8)$$

In an area without a magnetic field the motion of an electron is uniform linear and parallel to the X-Y plane, and therefore an electron passing the point $P_1$ ($l_1$, $dl_1$) runs straight and arrives at the point $P_2$. Here, the coordinates of the point $P_2$ are as follows.

$$P_2(x,y) = P_2(l_1 + D, dl_1 + D \tan\theta_1)$$

Here, D presents the interval between the edges of the magnetic field 106a and the magnetic field 107a. The electron which reaches the point $P_2$ is moved uniformly in a circular orbit of radius $r_2$ around the point $C_2$ by the magnetic field of the magnetic flux density $B_2$. An electron which reaches the point $P_3$ is biased a distance $dl_2$ toward the Y-axis from the point $P_2$. In other words, the distance of the bias from the X-axis when the electron passes point $P_3$ (in other words, the value of a Y coordinate) is as follows.

$$dl = dl_1 + D \tan\theta_1 + dl_2 \quad (9)$$

Also, when the difference of the point $P_3$ and the point $C_2$ toward the X-axis is $\Delta x$, because the point $P_2 P_2(x, y) = P_2(l_1 + D, dl_1 + D \tan\theta_1)$ and the point $P_3 P_3(x, y) = P_3(l_1 + D + l_2 - \Delta x, dl_1 + D \tan\theta_1 + dl_2)$ located on the circular orbit of radius $r_2$, the biased distance of electron $dl_2$ biased by magnetic flux density $B_2$ can be expressed as per Equation (10).

$$dl_2 = r_2 \cos\theta_2 - r_2 \cos\theta_1 = r_2\sqrt{1-\sin^2\theta_2} - r_2\sqrt{1-\sin^2\theta_1} \quad (10)$$
$$= r_2\sqrt{1-\left(\frac{\Delta X}{r_2}\right)^2} - r_2\sqrt{1-\left(\frac{l_2}{r_2}\right)^2}$$

Therefore, the distance of the bias dl from an X-axis when an electron passes the point $P_3$ is expressed by Equation (9) and Equation (10) as follows.

$$dl = r_1\left(1 - \sqrt{1-\left(\frac{l_1}{r_1}\right)^2}\right) + D\frac{l_1}{r_1 - r_1\left(1-\sqrt{1-\left(\frac{l_1}{r_1}\right)^2}\right)} + \quad (11)$$
$$r_2\sqrt{1-\left(\frac{\Delta X}{r_2}\right)^2} - r_2\sqrt{1-\left(\frac{l_2}{r_2}\right)^2}$$

Here, $$r_2 = \frac{mv}{eB_2} = \frac{m_0 v}{e\sqrt{1-\left(\frac{v}{c}\right)^2}} \times \frac{1}{B_2} \quad (12)$$

The electron moves straight and reaches the point $P_4$ on the plane of the X-ray target without being affected by the magnetic field after passing the point $P_3$. The tangential gradient of the point $P_3$ is given by the next equation.

$$\tan\theta_2 = \left[\frac{dy}{dx}\right]_{P_3} \quad (13)$$
$$= \frac{\Delta X}{l_3}$$
$$= \frac{\Delta X}{r_2 \cos\theta_2}$$
$$= \frac{\Delta X}{r_2\sqrt{1-\sin^2\theta_2}}$$
$$= \frac{\Delta X}{r_2\sqrt{1-\left(\frac{\Delta X}{r_2}\right)^2}}$$

Therefore, $$\theta_2 = \tan^{-1}\left(\frac{\Delta X}{r_2\sqrt{1-\left(\frac{\Delta X}{r_2}\right)^2}}\right) \quad (14)$$

When $\Delta x = 0$, in other words the point $P_3$ has the same X-coordinate as the central point $C_2$ of the circle, the tangent in the point $P_3$ on the circular orbit is $\theta_2 = 0$ in parallel to an X-axis. In other words, a high-speed electron can be incident in parallel to each medial axis of the target tube 104-1 through 104-n by controlling the voltage, using the electron gun 103 accelerating an electron and the magnetic flux density of the first deflection electromagnet 106 and the second deflection electromagnet 107.

Figure 4:
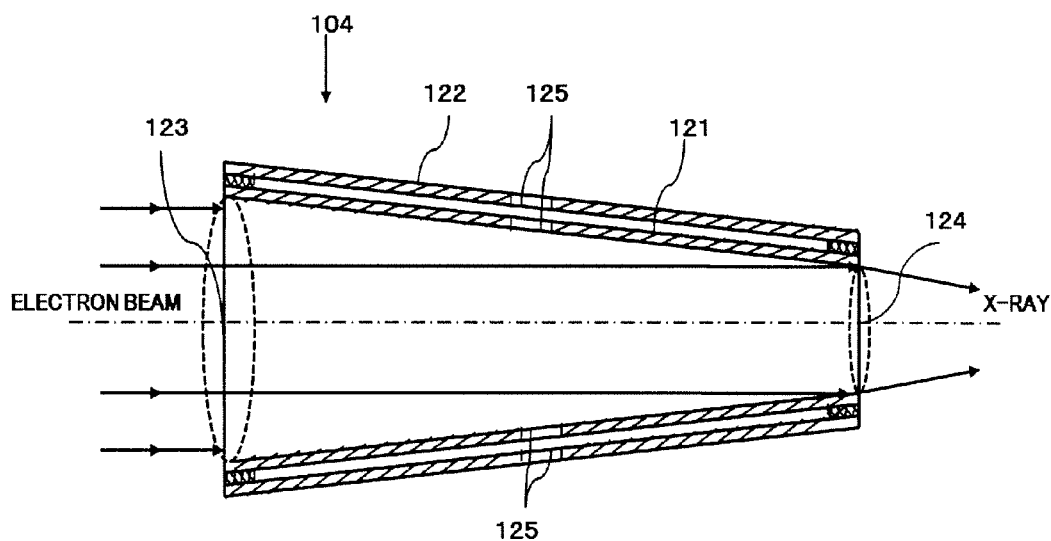
FIG. 4 is a configuration diagram of the X-ray target tube according to the preferred first embodiment of the present invention.

FIG. 4 shows the X-ray target tube according to the preferred first embodiment of the present invention. In FIG. 4, the X-ray target tube 104, patented by the present inventor as Japanese Patent No. 3795028, is comprised of a main body of the X-ray target tube 121 and a cover tube 122. The main body of the X-ray target tube 121 is formed of a metal with a heavy atomic weight, high melting point, high chemical stability, and superior thermal radiation characteristic, for example Au, W, MO, Pt, or Re. The main body of the X-ray target tube 121 has the shape of an extremely thin truncated cone, in which the diameter of an inlet aperture 123 is 1 mm, the diameter of an outlet aperture 124 is 0.5 mm, and the overall length is 100 mm.

The high energy electron beams are radiated by the electron gun 103 in the form of doughnuts whose outside diameter is approximately equal to the inlet aperture 123 and inside diameter is approximately equal to the outlet aperture 124. X-rays are irradiated by high energy electron beams colliding with the inner wall of this X-ray target tube. The generated X-rays are totally reflected and are irradiated as X-rays of extremely small radiation angular degree from the outlet aperture 124 because the incline of the inner wall of the X-ray target tube 121 is 0.143239 degree, since the diameter of the target tube narrows to 0.25 mm over its length of 100 mm.

The outside of the main body of the X-ray target tube 121 is covered with the cover tube 122. Holes 125 to discharge the gas which is generated by the collision of high energy electron beams are made in the main body of the X-ray target tube 121 and the cover tube 122. Even more particularly, the heat which is generated by the collision of high energy electron beams is cooled by forced air-cooling or water-cooling.

Figure 5:
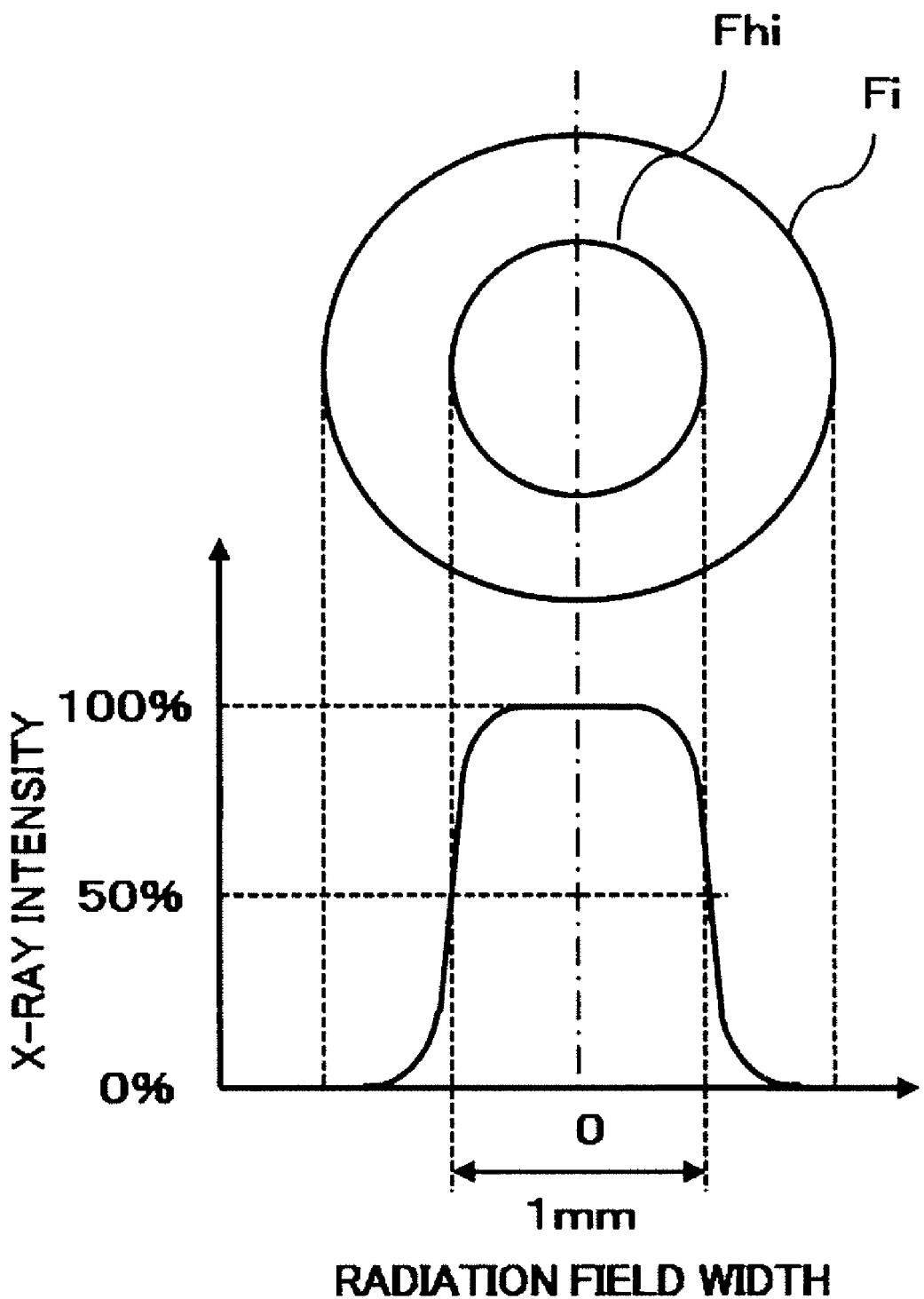
FIG. 5 is a diagram describing the radiation field of the X-ray target tube according to the preferred first embodiment of the present invention.

FIG. 5 shows the dose distribution in the radiation field of the X-ray target tube according to the preferred first embodiment of the present invention. In FIG. 5, the shape of the radiation field Fi of the X-ray target tube 104 is approximately circular at a lesion assumed to be positioned 50 cm from the outlet aperture 124. The X-ray intensity is approximately constant near a center of the radiation field, but the intensity decays sharply to zero at the periphery of the radiation field. In the radiation field Fi of the X-ray target tube 104, the area where the X-ray intensity is half the maximum, namely the radiation field Fhi of ½ width, is a circle the diameter of which is approximately 1 mm.

Figure 6:
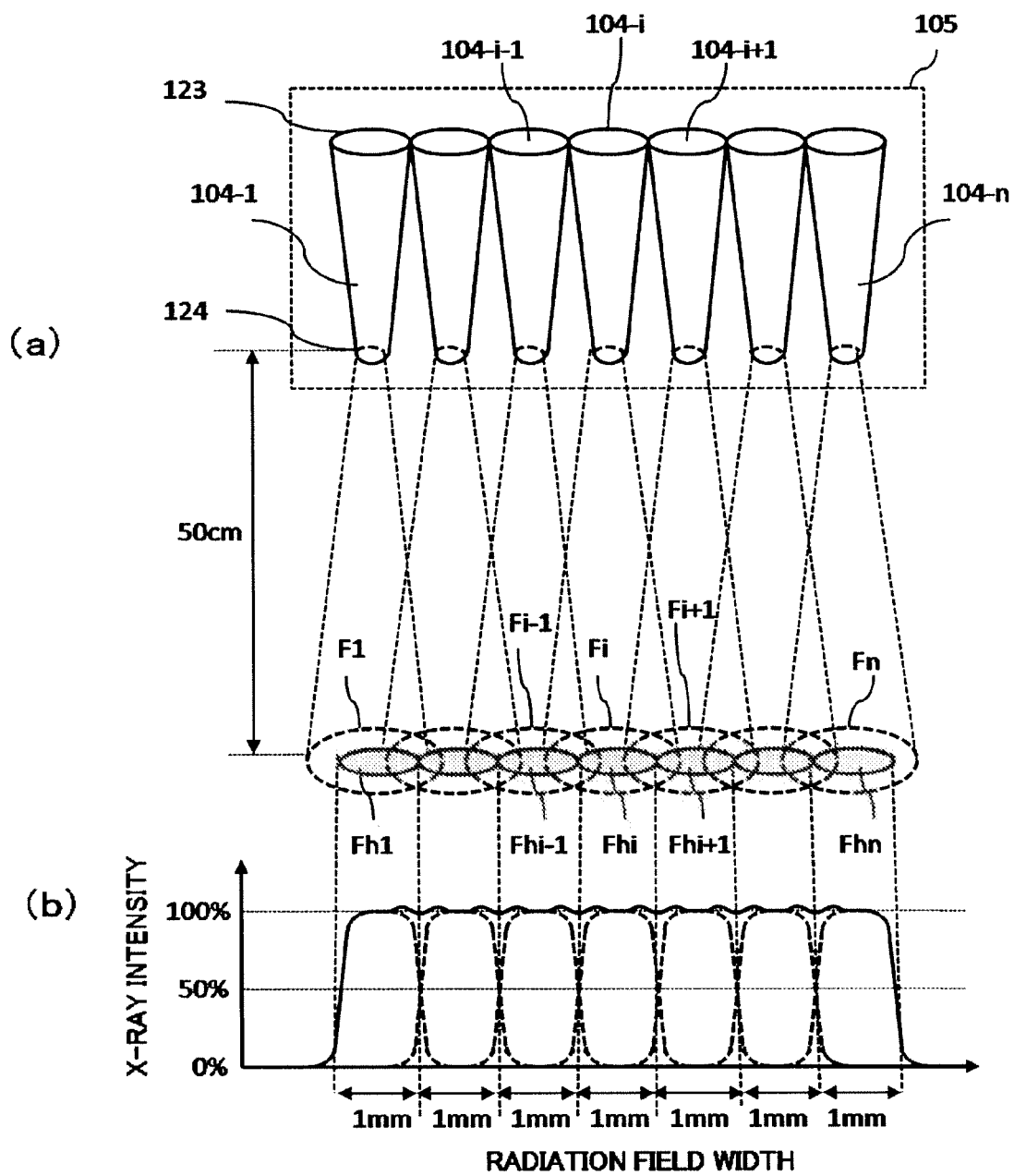
FIG. 6 is a diagram describing the radiation field of the X-ray target tube array according to the preferred first embodiment of the present invention.

FIG. 6 shows the radiation field of the X-ray target tube array according to the preferred first embodiment of the present invention. FIG. 6($a$) shows the relationship between the radiation field of the X-ray target tube array 105 and the radiation field of each X-ray target tube 104 comprising the X-ray target tube array 105. FIG. 6($b$) shows the dose distribution when X-rays of the same intensity are radiated from each X-ray target tube. In FIG. 6($a$), the X-ray target tube array 105 is comprised of the plurality of X-ray target tubes 104-1 through 104-$n$ arranged in a line, so that the radiation fields of ½ width Fh1-Fhn for each X-ray target tubes 104-1 through 104-$n$ are formed without any clearance therebetween adjacently at a predetermined distance, for example, 50 cm from the outlet aperture 124, which is the assumed distance of the lesion of a patient from the outlet aperture 124. More specifically, the X-ray target tube array 105 is comprised of the plurality of X-ray target tubes 104-1 through 104-$n$ arranged so that the radiation field Fhi, which is ½ width of the X-ray target tube 104-$l$, adjoins the radiation field Fhi-1, which is ½ width of the X-ray target tube 104-$i$+1, and the radiation field Fhi-1, which is ½ width of the X-ray target tube 104-$i$−1. Thus, the radiation field of the X-ray target tube array 105 is comprised of radiation fields F1 through Fn, which are the radiation fields of the X-ray target tubes 104-1 through 104-$n$. Hence, as shown in FIG. 6($b$), when the radiation intensity of each X-ray target tube is the same, the whole X-ray radiation intensity can be approximately equal throughout the whole radiation field. For example, the X-ray target tube array which can irradiate an area of 50×50 mm is comprised as follows. When the radiation field of ½ width at a distance of 50 cm from the outlet aperture of one X-ray target tube is assumed to be a circle of a diameter of 1 mm, a slim rectangular radiation field of 1×50 mm is formed by arranging in line 50 X-ray target tubes 104-1 through 104-50. The radiation field of 50×50 mm is formed by repeating 50 times to translate the radiation field of 1×50 mm by 1 mm after irradiation. As for the method of translation of the radiation field, there are two methods: moving the X-ray target array and moving the irradiated object.

Figure 7:
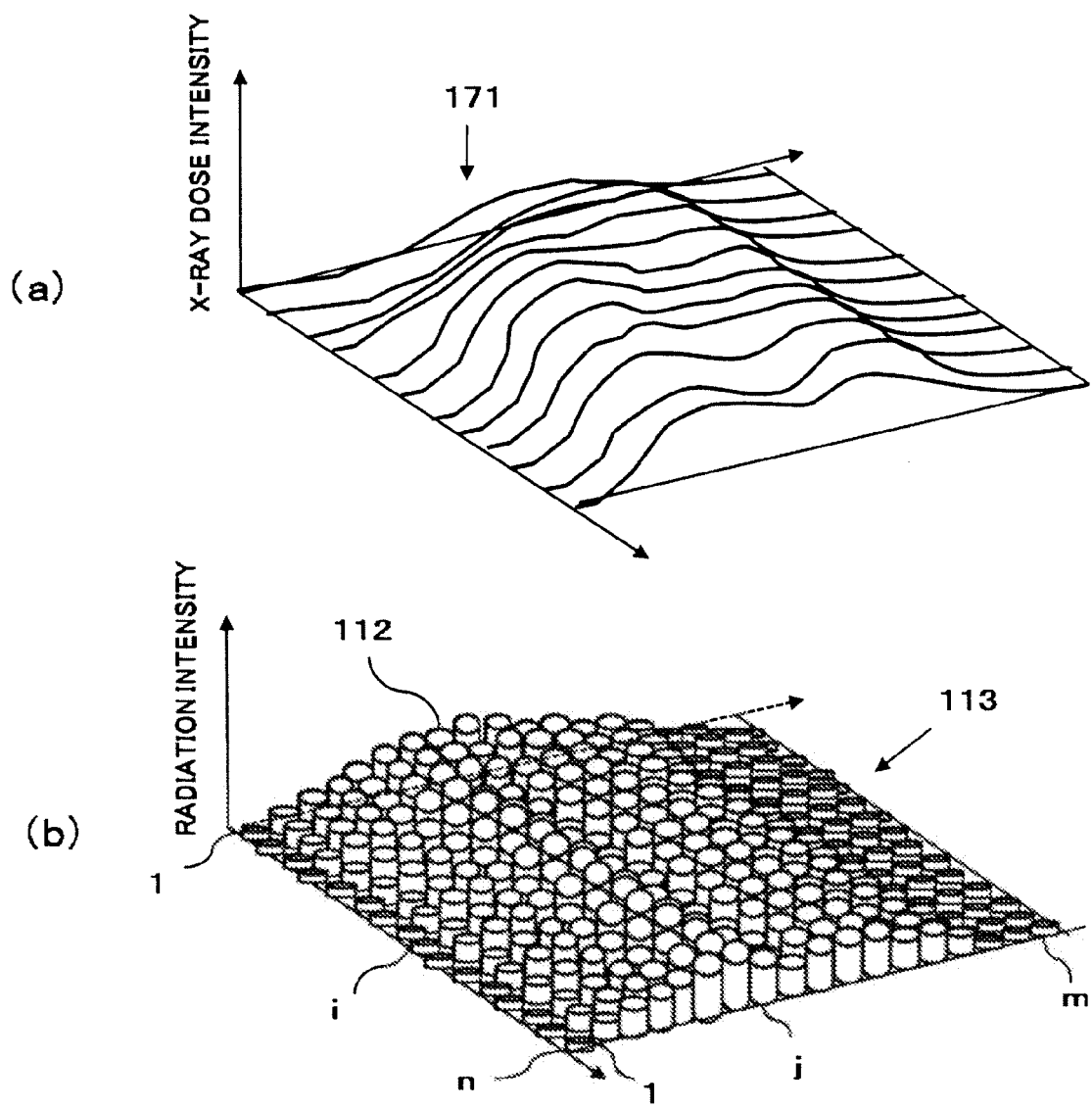
FIG. 7 is a diagram describing the radiation intensity data of the treatment field and the radiation intensity data of the radiation field according to the preferred first embodiment of the present invention.

The X-ray dose intensity data of the treatment field and the radiation intensity data of the radiation field according to the preferred first embodiment of the present invention are shown in FIG. 7. In IMRT, the dose required for treatment of the lesion portion and the ideal dose distribution which takes into account the permissible dose for neighboring normal cells is set first. Next, the shape of the radiation field, the radiation direction, and the dose intensity of each radiation field subdivision are input into the therapeutic apparatus as treatment plan data. FIG. 7($a$) shows the two-dimensional dose intensity distribution which is required for treatment of the lesion portion viewing from direction 171. FIG. 7 ($b$) shows the radiation intensity data 113 of a treatment field produced according to the two-dimensional dose intensity distribution of the lesion portion in FIG. 7($a$). The treatment field radiation intensity data 113 is subdivided into radiation intensity data 112 (i, j) for every X-ray target tube 104-1 through 104-$n$.

Figure 8:
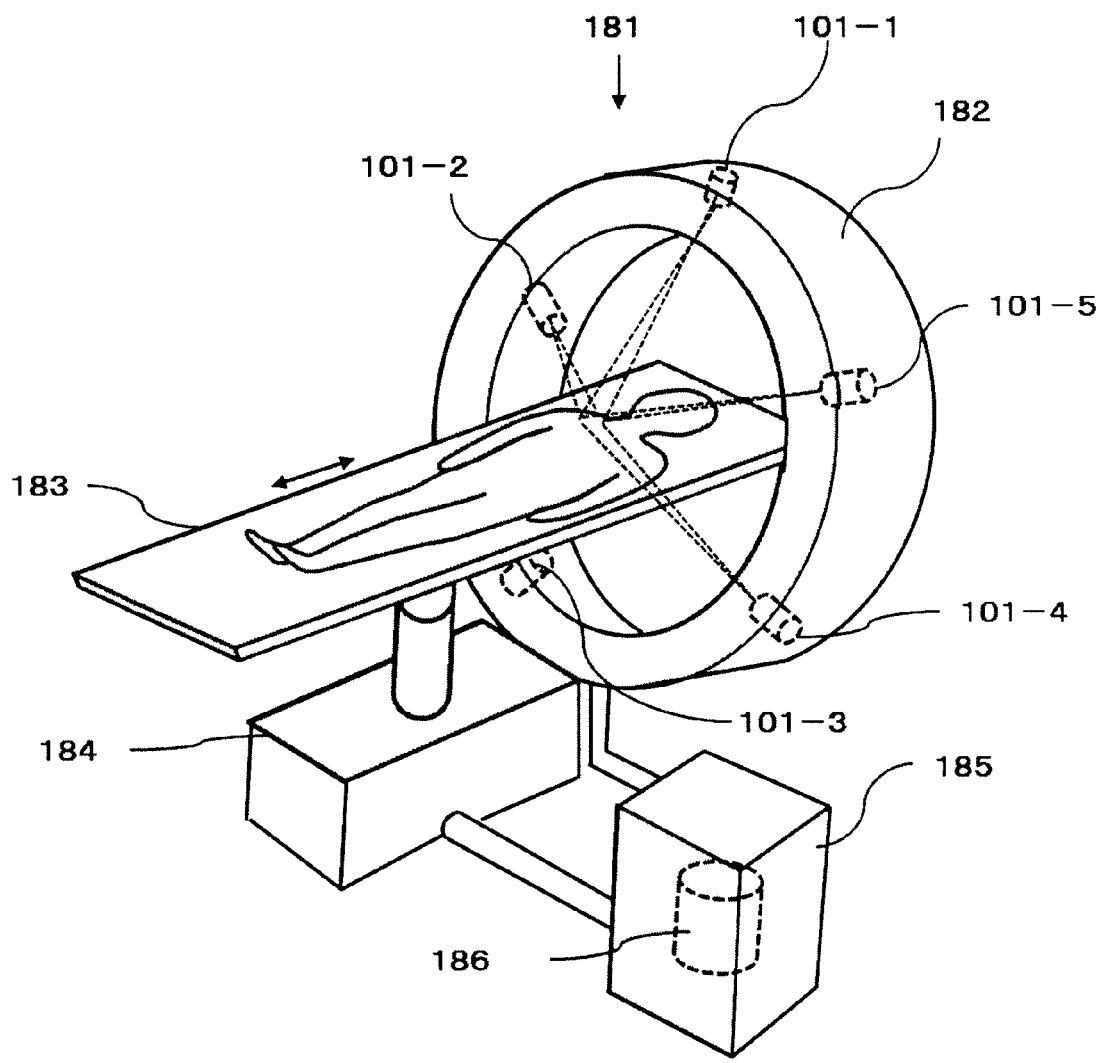
FIG. 8 is a perspective view which shows a configuration example of the X-ray therapeutic apparatus including the X-ray generator according to the preferred first embodiment of the present invention.

FIG. 8 shows the perspective view of the X-ray therapeutic apparatus with the X-ray generator according to the preferred first embodiment of the present invention mounted therein. As shown in FIG. 8, an X-ray therapeutic apparatus 181 comprises five X-ray generators 101-1 through 101-5 at five places on an O-type arm 182, which are at the top, the upper right, the lower right, the upper left and the lower left; a treatment couch 183 on which a patient lies located in an inner side of the O-type arm 182; a transfer unit 184 moving the treatment couch 183 horizontally; and a control unit 185 to control operation of the transfer unit 184. The X-ray radiation apertures of X-ray generators 101-1 through 101-5 are attached for the lesion portion of the patient who is fixed on the treatment couch 183. The control unit 185 stores a treatment control program 186, a radiation control program, radiation intensity data of the treatment field and radiation intensity data of the radiation field. The X-ray therapeutic apparatus irradiates from five X-ray generators 101-1 through 101-5 simultaneously while moving the treatment couch 183 by 1 mm depending on execution of the treatment control program 186, and the X-radiation therapy is carried out.

Figure 9:
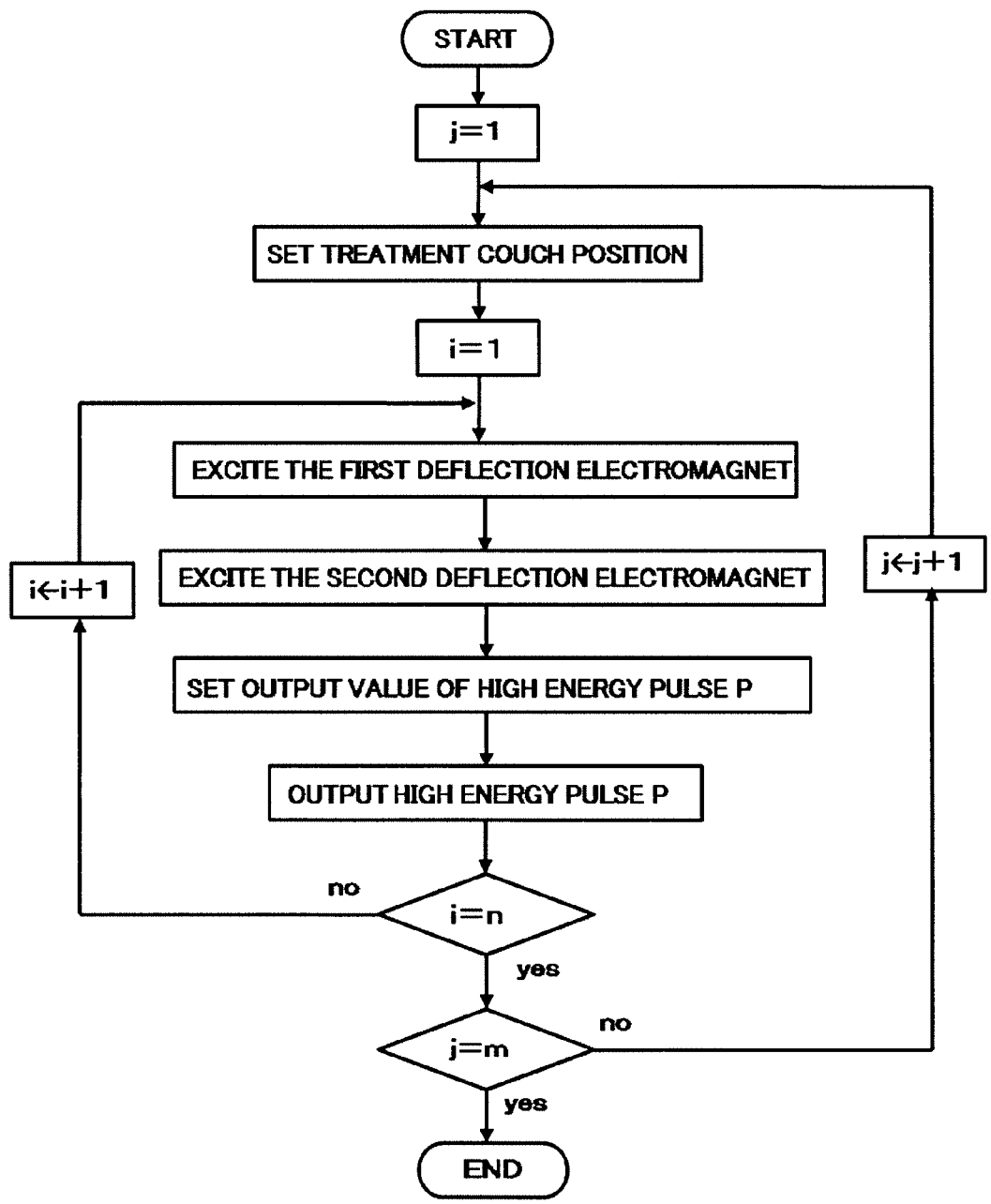
FIG. 9 is a flow chart which shows the routine of a radiation control program of the X-ray generator according to the preferred first embodiment of the present invention.

FIG. 9 is a flow chart showing the routine of the radiation control program of the X-ray generator according to the preferred first embodiment of the present invention. In the exposition of the flow chart of FIG. 9, the number of pieces of the radiation intensity data 112 comprising the treatment field radiation intensity data 113 shown in FIG. 7($b$) is m, the number of X-ray target tubes 104 comprising the X-ray target tube array 105 is n, the X-ray target tube 104 number is i, and the radiation field radiation intensity data 112 number is j. The X-ray irradiation is carried out from the radiation intensity data 112 (1,1) to 112 (n, 1), the treatment couch 183 is moved 1 mm, and the X-ray radiation is carried out from 112 (1,2) to 112 (n, 2). After this, the X-ray radiation is carried out to 112 (n, m) according to the radiation control program 111 by repeating the same sequence. Firstly, as shown in the flow chart of FIG. 9, j=1, i=1 are set so that the X-ray radiation start to irradiate from the X-ray target tube 104-1 of i=1 to the X-ray target tube 104-$n$ of i=n in turn according to the radiation intensity data 112 for radiation field of j=1 of the treatment field radiation intensity data 113. The first deflection electromagnet 106 is excited so that the high energy electron beams radiated from the electron gun 103 turn toward the inlet aperture 123 of the i-th X-ray target tube 104-$i$ of the X-ray target tube array 105. The second deflection electromagnet 107 is excited by the exciting current of reverse phase to that for the first deflection electromagnet 106, so that the electron beam deflected with the first deflection electromagnet 106 penetrates parallel to the medial axis of the X-ray target tube 104-$i$. In the radiation field radiation intensity data 112 of j-th line, the width of the high energy pulse is set according to the radiation dose set for the i-th X-ray target tube 104-$i$. Subsequently, the high energy pulse is output at the suitable timing. As a result of this, X-rays with the desired intensity irradiated the lesion portion with the X-ray target tube 104-$i$. This series of operations is the same for the X-ray generators 101-1 through 101-5 in FIG. 8. After the high energy pulses have been output, the radiation control program judges whether i=n, and if still i≠n, as i=i+1, the excitation of the electromagnet, the output condition setting of the high energy pulse, and the pulse outputting are repeated. If i=n, the radiation control program judges next whether j=m, and if j≠m, the radiation control program is executed for the j+1st line of the radiation field radiation intensity data 112 as j=j+1. Initially, the treatment couch 183 is moved 1 mm and the X-ray target tube 104-1 is set up. After this, the excitation of the electromagnet, the setting of the output condition for the high energy pulse, and the outputting of the pulse are repeated until i=n. The above-mentioned sequence is repeated until i=n, j=m.

Figure 10:
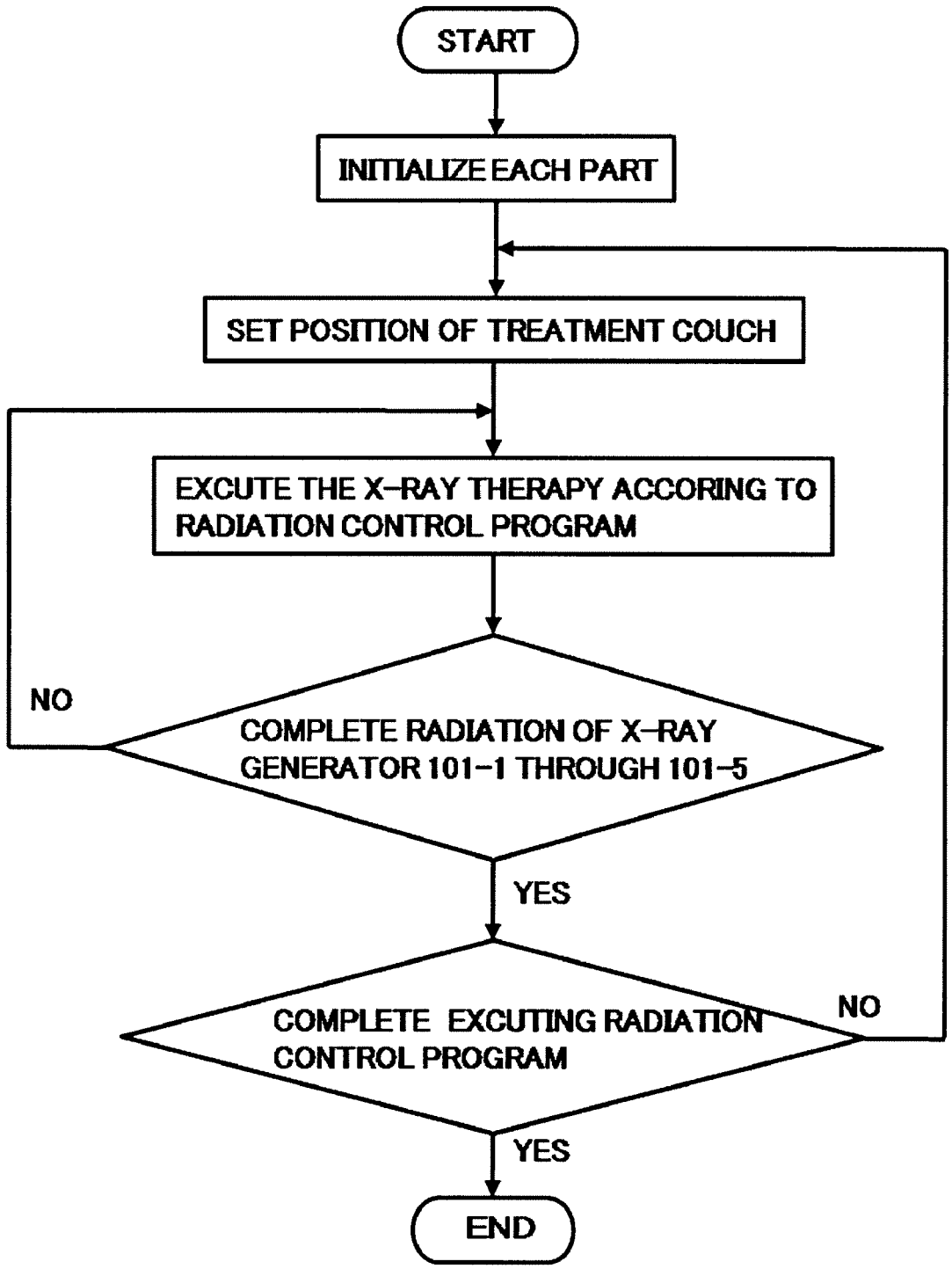
FIG. 10 is a flow chart which shows the routine of a treatment execution program of a control unit according to the preferred first embodiment of the present invention.

FIG. 10 is a flow chart showing the routine of the treatment execution program of the control unit according to the preferred first embodiment of the present invention. As shown in FIG. 10, initially the X-ray generators 101-1 through 101-5 and each part of the apparatus are initialized and the position of the treatment couch is set in accordance with set the values of i and j of the radiation control program 111. After this, the X-ray therapy is executed according to the radiation control program 111. It is judged whether the radiation control program execution of the X-ray generators 101-1 through 101-5 is completed at each irradiation, and the sequence is continued if the program execution is not yet completed. As for the treatment, it is finished when the radiation control program execution of all X-ray generators is completed.

Figure 11:
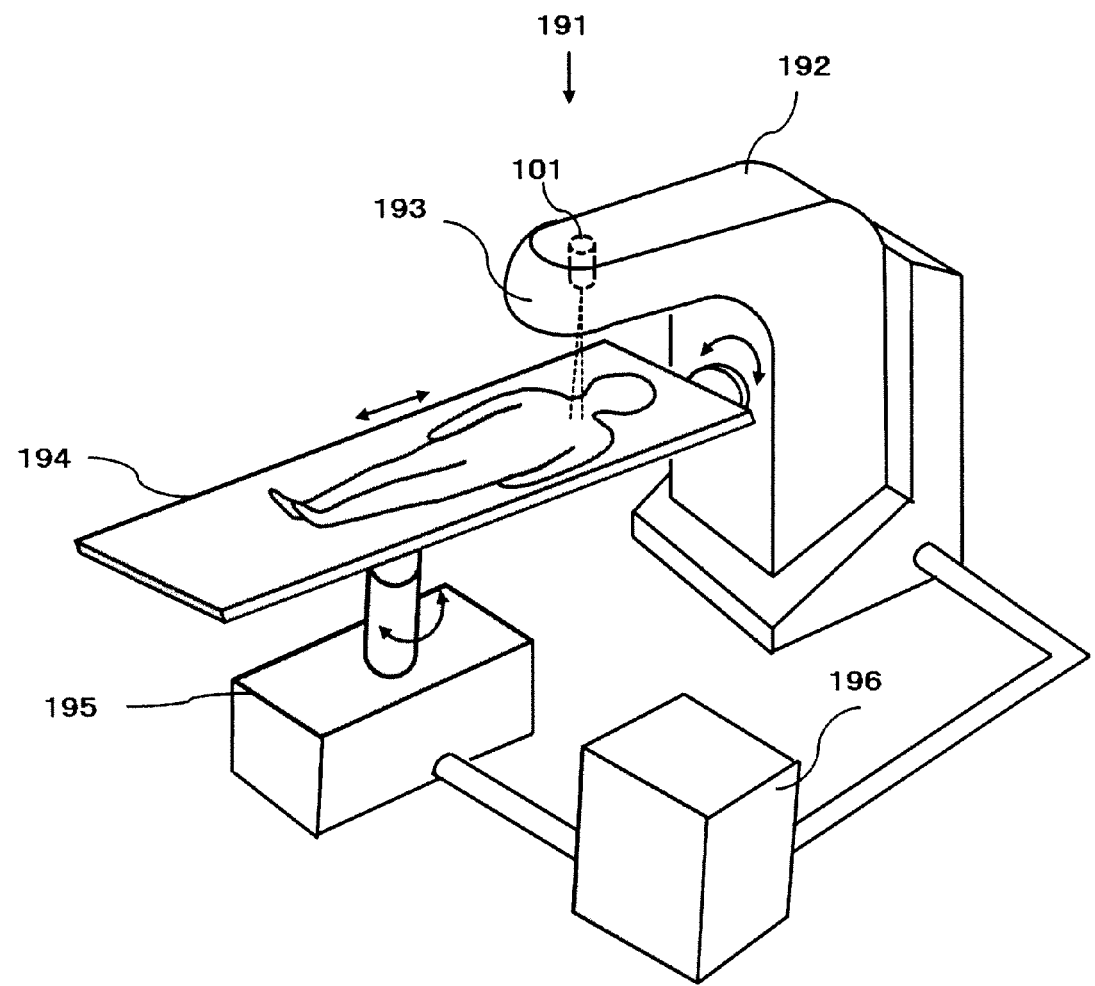
FIG. 11 is a perspective diagram which shows an example of another X-ray therapeutic apparatus including the X-ray generator according to the preferred first embodiment of the present invention to a gantry.

FIG. 11 shows the perspective view of another X-ray therapeutic apparatus in which the X-ray generator according to the preferred first embodiment of the present invention is mounted on a gantry. As shown in FIG. 11, the X-ray therapeutic apparatus 191 mounts the X-ray generator 101 on a radiation head 193 of the gantry 192 used for the conventional radiation therapy apparatus.

The X-ray therapeutic apparatus 191 comprises a treatment couch 194 to put a patient on, a transfer unit 195 moving the treatment couch 194 in the horizontal direction, and a control unit 196 which is connected to the X-ray generator 101 and the transfer unit 195, to carry out X-ray therapy. The X-ray therapeutic apparatus 191, as with conventional IMRT, turns the gantry 192 around the treatment couch 194 on which the patient is put while concentrating on the isocenter of the lesion portion. The treatment couch 194 moves horizontally and perpendicularly to the X-ray target tube array 105 of the X-ray generator 101 by the transfer unit 195. The X-ray generator 101 irradiates X-rays in synchrony with movement of the treatment couch 194. The treatment field radiation intensity data 113 is divided so as to match the rotation angle of the gantry 192 to the two-dimensional dose distribution 171 required for the treatment of the lesion portion for the patient. The treatment field radiation intensity data 113 is set for each rotation angle of the gantry 192. Meanwhile, the treatment couch 194 is irradiated with X-rays corresponding to the radiation dose and moved by 1 mm with respect to the X-ray generator 101 by the transfer unit 195.

As explained in detail above, the X-ray generator 101 according to the foregoing detailed description of the preferred first embodiment is comprised of the electron gun 103, the first deflection electromagnet 106, the second deflection electromagnet 107, and the X-ray target tube array 105. The electron gun 103 radiates high energy electron beams with a high energy pulse output from the power source 108. The first deflection electromagnet 106 and the second deflection electromagnet 107 change the direction of high energy electron beams so that the high energy electron beams are incident in parallel with the medial axis of X-ray target tubes 104-1 through 104-$n$, and the high energy electron beams are incident on the X-ray target tubes 104-1 through 104-$n$ in turn. The X-ray target tube array 105 is comprised of a bundle of a plurality of X-ray target tubes so that fields F1 through Fn of the X-ray target tubes 104-1 through 104-$n$ radiating X-rays by the collision of high energy electron beams is continuous. The radiation intensity of each X-ray target tube 104-$i$ and the width of the high energy pulse output from the power source 108 are set by the radiation intensity data 113 stored in the controller 109. As for the timing to output the high energy pulse and the timing to excite the first deflection electromagnet 106 and the second deflection electromagnet 107 so that the electron beam generated by pulse is aligned with the position of a predetermined X-ray target tube 104-$i$, these are controlled by the radiation control program 111. In this way, the X-ray generator 101 according to detailed description of the preferred first embodiment can obtain an X-ray dose distribution intensity modulated corresponding to the X-ray dose which is desired for treatment of each part of the lesion portion. According to detailed description of the preferred first embodiment, the radiation fields F1-Fn of X-ray target tubes 104-1-104-$n$ are a bundle of several field are continuous in a lesion of the patient, and therefore the radiation field of the X-ray target tube array 105 becomes continuous. According to detailed description of the preferred first embodiment, the radiation fields Fh1 through Fhn of ½ width of X-ray target tubes 104-1 through 104-$n$ are bundled so that the field of ½ width continues in a lesion portion of the patient, and therefore the composed radiation field of the X-ray target tube array 105 is of uniform radiation intensity. In the X-ray generator of the detailed description of the preferred first embodiment above, the electron gun 103 outputs high energy electron beams when high energy pulses p-1 through p-n with pulse widths corresponding to the required radiation dose are input. The electron beam collides with the inner walls of the X-ray target tubes 104-1 through 104-$n$, and X-ray beams x-1 through x-n are irradiated. The X-ray generator 101 of the detailed description of the preferred first embodiment is different from the conventional X-ray generator repeating multiple X-ray irradiations using a multi-leaf collimator, and the two-dimensional dose distribution for the treatment can be obtained immediately because it is not necessary to adjust a multi-leaf collimator for the X-ray radiation with detailed description of the preferred first embodiment, and the time needed for treatment can be shortened, thereby easing the burden on the patient.

Detailed Description of a Preferred Second Embodiment

Figure 12:
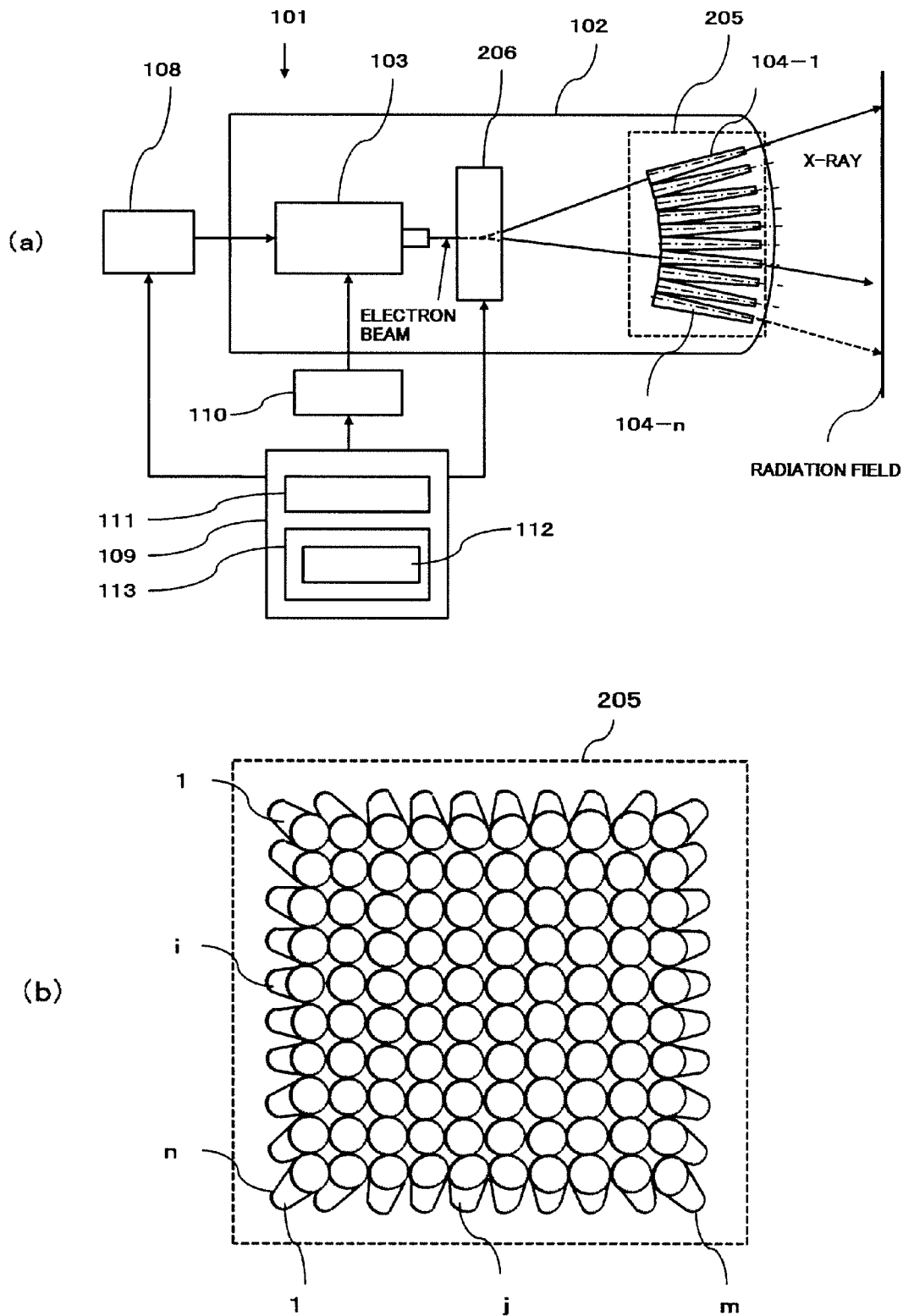
FIG. 12 is a block diagram of the X-ray generator according to a preferred second embodiment of the present invention.

Next, the X-ray generator according to a preferred second embodiment of the present invention is explained. FIG. 12($a$) shows the configuration of the X-ray generator according to the preferred second embodiment of the present invention. Constituent parts that are the same as those of the detailed description of the preferred first embodiment are shown with the same reference numerals. The characteristic of the X-ray generator according to this detailed description of the preferred second embodiment is to irradiate the high energy electron beams while scanning to the X-ray target tube array 205 arranging the X-ray target tube 104 in a matrix state as shown in FIG. 12(b). Even more particularly, a characteristic of the X-ray generator according to this detailed description of the preferred second embodiment is that the high energy electron beams deflected by an deflection electromagnet 206 are able to be incident parallel to a medial axis of each X-ray target tube 104 (i, j) of the X-ray target tube array 205 by changing the shape of the inlet aperture plane of the X-ray target tube array 205 radially. As a result of this arrangement, for example, the radiation field of the X-ray target tube array 105 can be formed radially to 50×50 mm at a position 50 cm away from the outlet aperture. To realize the X-ray generator according to this detailed description of the preferred second embodiment, the first deflection electromagnet 106 and the second deflection electromagnet 107 deflecting one dimensionally the direction of high energy electron beams in the X-ray generator according to the detailed description of the preferred first embodiment are replaced by a quadrupole electromagnet 206 that makes two-dimensional deflection is possible.

Figure 13:
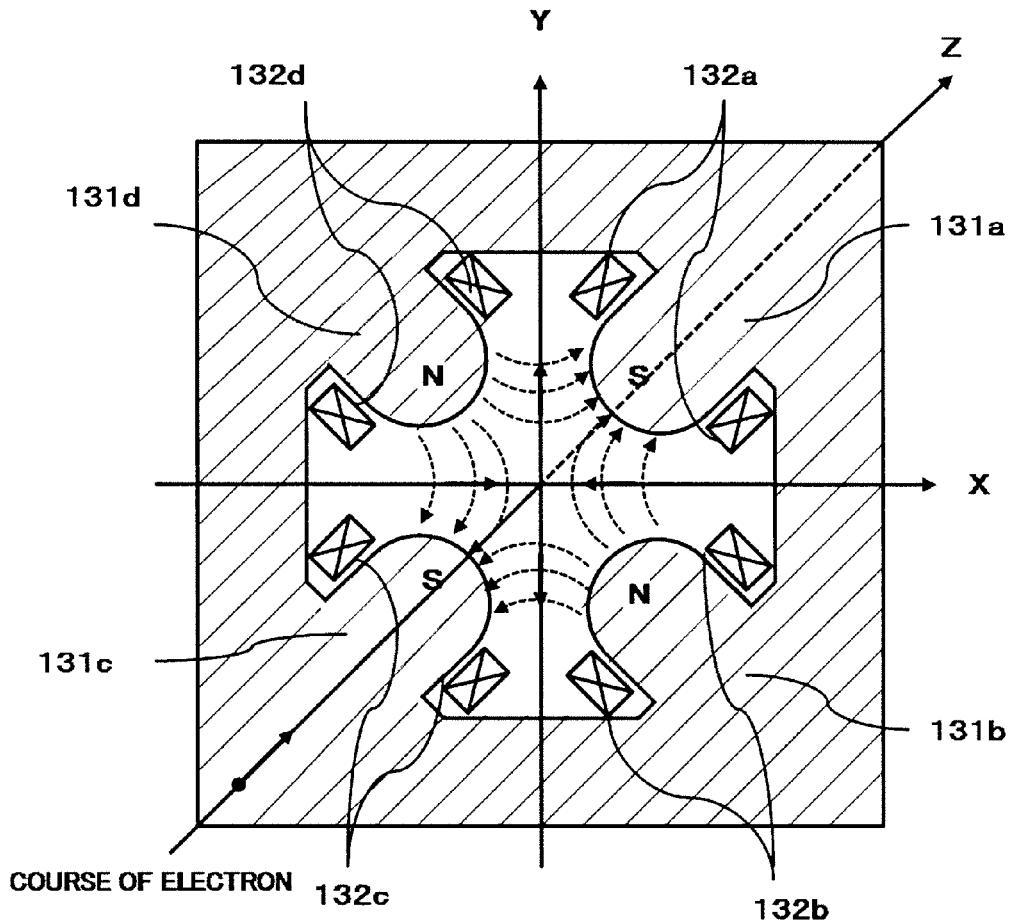
FIG. 13 is a cross-sectional view of a quadrupole electromagnet according to the preferred second embodiment of the present invention along a plane perpendicular to the direction of the electron beam.
Figure 14:
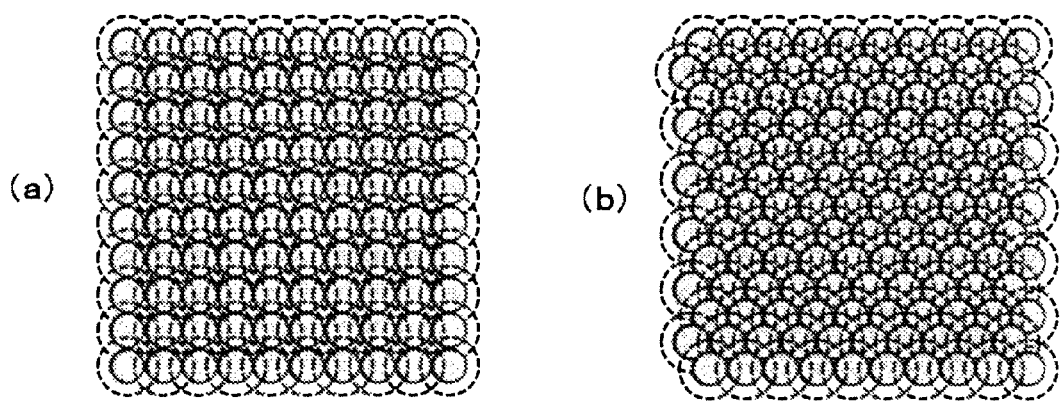
FIG. 14 is a diagram describing the radiation field of the X-ray target array according to the preferred second embodiment of the present invention.
Figure 15:
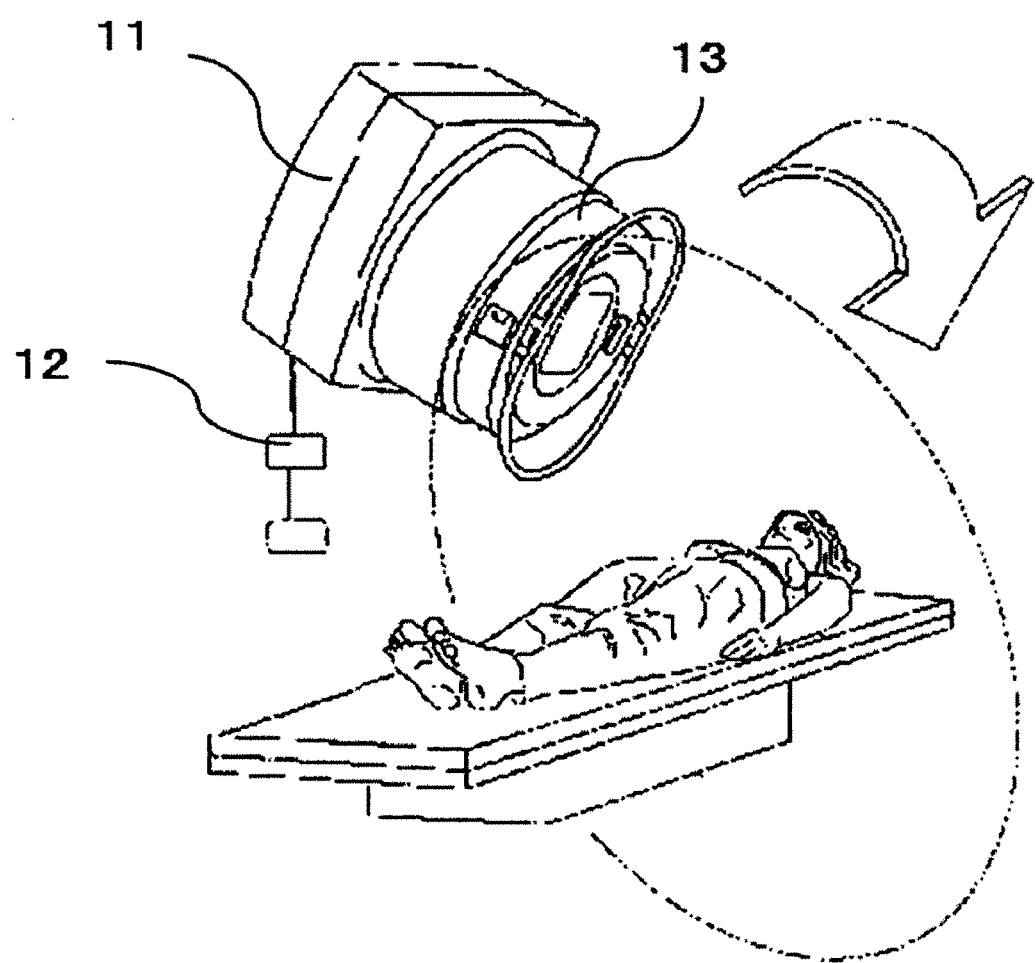
FIG. 15 is a perspective view which shows a conventional intensity modulated arc therapy with dynamic multi-leaf collimation.

FIG. 13 shows cross-sectional view cut across the quadrupole electromagnet with the face (X-Y axial plane) perpendicular to the direction (Z-axis course) of the electron beam. In FIG. 13, the quadrupole electromagnet consists of the four magnetic cores 131a through 131d and the magnetizing coils 132a through 132d wound around each magnetic core. A magnetic field is generated in the direction shown with the broken line arrow in FIG. 13 by sending an exciting current through the coil. The direction of the magnetic field can be set to the opposite direction by reversing the polarity of the exciting current. In FIG. 13, when high energy electron beams are incident on the Z-axis direction (from front to back), a Lorentz force works in the direction of the solid line arrow. Thus, by control of the excitation current magnitude and the polarity, the course of electrons can be deflected in any arbitrary direction of the X-Y axial plane. The electrons via the magnetic field of the quadrupole electromagnet go straight on, and reach the inlet aperture plane of the X-ray target tube array 205. The X-ray target tube 104 (i, j) is arranged in a matrix state as shown in FIG. 12(b). More particularly, the inlet aperture plane is placed radially so that the electrons which went straight on after being deflected by the quadrupole electromagnet are incident on a medial axis of the X-ray target tube 104 (i, j) horizontally. Thus, the X-rays irradiating from the X-ray target tube array 205 are irradiated radially and the radiation field is formed as shown in FIG. 14. The radiation field of each target tube 104 (i, j) comprising the radiation field of the X-ray target tube array 205 is formed so that the radiation fields of ½ width are adjacent as in the first embodiment.

In the detailed description of the preferred second embodiment, because the radiation of each of the X-ray target tubes 104 (i, j) is adjacent to any other in a matrix state. Of the ways they are adjacent, a case in which ½ width of the radiation field adjoins at four places as shown in FIG. 14(a) and at six places as shown in FIG. 14(b) are considered. For example, in a case in which a radiation field of 50×50 mm is formed at a position 50 cm from the outlet aperture of the X-ray target tube array 205 and the diameter of ½ width of the X-ray target tube 104 is assumed to be 1 mm, when the configuration adjoining at four places with adjacent X-ray target tubes is adopted, the X-ray target tube array 105 is comprised of 250 X-ray target tubes. The radiation intensity of each X-ray target tube 104 (i, j) is based on the radiation field radiation intensity data 112 set beforehand as in the detailed description of the preferred first embodiment. The order of scans when the X-rays are radiated is selectable, such as scanning from the center to the periphery of the radiation field, scanning from the circumference to the center, and scanning in rows or columns from one corner to the other opposite corner, depending on use conditions. As discussed above, according to the detailed description of the preferred second embodiment, because the X-ray target tubes are arranged radially, the radiation field can be formed over a wide plane. Thus, treatment time can be shortened compared to the X-ray therapeutic apparatus according to the detailed description of the preferred first embodiment without moving the X-ray generator or the treatment couch on which a patient is put, and an X-ray therapeutic apparatus which is suitable for IMRT can be provided.

The X-ray generator according to the present invention and the X-ray therapeutic apparatus which uses the X-ray generator can be utilized as an X-ray therapeutic apparatus which is suitable for IMRT in the medical field. The X-ray generator according to the present invention can be utilized as a nondestructive inspection system and an X-ray analysis device in the industrial field.

What is claimed is:

1. An X-ray generator, comprising:
  a power source outputting high energy pulses;
  an electron source radiating high energy electron beams from the high energy pulses;
  a microwave source supplying a high voltage microwave to the electron source;
  an X-ray source comprising a bundle of a plurality of X-ray tubes radiating X-rays by a collision of the high-energy electron beams, arranged to form a continuous radiation field of the plurality of X-ray tubes;
  a deflection means deflecting the direction of the high energy electron beams so that the high energy electron beams are incident in parallel to the medial axis of the X-ray tubes, and are incident on the X-ray tubes sequentially;
  a data setting unit that sets the radiation intensity of the X-ray tubes so that a predetermined dose distribution is obtained in the field of the X-ray tubes; and
  a control means setting the high energy pulse width according to the radiation intensity data, synchronizing a timing to output the high energy pulse and a timing to radiate the electron beams and a timing to excite the deflection means,
  the control means selectively setting the high energy pulse width separately for each X-ray tube of the plurality of X-ray tubes.

2. The X-ray generator of claim 1, wherein the deflection means comprises a first deflection electromagnet selectively deflecting the high energy electron beam to an inlet aperture of any one of the plurality of X-ray tubes and a second deflection electromagnet deflecting the high energy electron beams deflected by the first deflection electromagnet so that the high energy electron beams are incident in parallel to the medial axis of the X-ray tubes.

3. The X-ray generator of claim 1, wherein the X-ray source comprises the X-ray tubes arranged in a line, and wherein the high energy electron beams are sequentially radiated from one end of the X-ray tubes to the other opposite end.

4. The X-ray generator of claim 1, wherein the X-ray source comprises the X-ray tubes arranged in a matrix, and wherein the outlets of the X-ray tubes are separated from each other to cause the X-rays radiated from the outlets of the X-ray tubes to spread widely.

5. The X-ray generator of claim 1, wherein the X-ray tube comprises a truncated cone shape having a smaller diameter of an outlet aperture than an inlet aperture, wherein at least a portion of an inner wall of the X-ray tube is tapered so as to narrow toward the outlet aperture, and wherein the inner wall of the X-ray tube acts as an X-ray target tube radiating X-ray beams by the collision of high energy electron beams with the inner wall of the X-ray tube.

6. An X-ray therapeutic apparatus, comprising the X-ray generator of claim 1, wherein one or more of the X-ray generators are installed in different positions of a three-dimensional space including a treatment couch, so that X-rays are radiated intensively on a lesion portion of a patient fixed on the treatment couch in the space.

7. An X-ray therapeutic apparatus, comprising the X-ray generator of claim 1, wherein the X-ray therapeutic apparatus is able to vary a relative position of a lesion portion of a patient fixed on a treatment couch and wherein the X-ray generator is installed in an X-ray head, so as to radiate X-rays to the lesion portion of the patient.

8. The X-ray generator of claim 1, wherein the X-ray tube comprises a truncated cone shape having a smaller diameter of an outlet aperture than an inlet aperture, wherein at least a portion of an inner wall of the X-ray tube is angled with respect to the medial axis of the X-ray tube, and wherein the inner wall of the X-ray tube acts as an X-ray target tube radiating X-ray beams by the collision of high energy electron beams with the inner wall of the X-ray tube.

9. The X-ray generator of claim 1, wherein the X-ray source comprises the X-ray tubes arranged in a matrix, and the X-rays are sequentially radiated from one corner of the matrix of X-rays tubes to the other diagonally opposite corner.

10. The X-ray generator of claim 1, wherein the X-ray source comprises the X-ray tubes arranged in a matrix, and the X-rays are sequentially radiated starting from a center of the matrix and proceeding outward toward a periphery of the matrix.

11. The X-ray generator of claim 1, wherein the X-ray source comprises the X-ray tubes arranged in a matrix, and the X-rays are sequentially radiated starting from a periphery of the matrix and proceeding toward a center of the matrix.

12. The X-ray generator of claim 5, wherein the slope of the taper of the inner wall of the X-ray tube is approximately 0.14 degrees.

13. An X-ray generator, comprising:
a power source outputting high energy pulses;
an electron source radiating high energy electron beams from the high energy pulses;
a microwave source supplying a high voltage microwave to the electron source;
an X-ray source comprising a bundle of a plurality of X-ray tubes radiating X-rays by a collision of the high-energy electron beams, arranging to continue the radiation fields of the X-ray tubes;
a deflection means deflecting the direction of the high energy electron beams so that the high energy electron beams are incident in parallel to the medial axis of the X-ray tubes, and are incident on the X-ray tubes sequentially;
a data setting unit that sets the radiation intensity of the X-ray tubes so that the predetermined dose distribution is obtained in the field of the X-ray tubes; and
a control means setting up the high energy pulse width according to the radiation intensity data, synchronizing a timing to output the high energy pulse and a timing to radiate the electron beams and a timing to excite the deflection means,
wherein the X-ray source comprises the X-ray tubes arranged so that radiation fields of ½ width for the maximum radiation intensity are adjacent in succession.

14. A method of modulating a radiation intensity of X-rays generated by an X-ray generator for therapeutic use without using a multi-leaf collimator, comprising the steps of:
outputting high energy pulses from a power source;
radiating high energy electron beams from the high energy pulses using an electron source;
deflecting the direction of the high energy electron beams so that the high energy electron beams are incident in parallel to the medial axis of a plurality of X-ray tubes serving as an X-ray source, and are incident on the X-ray tubes sequentially;
generating X-rays from the X-ray tubes by collision of the high energy electron beams with inner walls of the X-ray tubes to generate a continuous X-ray radiation field from the X-ray tubes;
setting the radiation intensity of the X-ray tubes so that a predetermined dose distribution is obtained for the field of the X-ray tubes using radiation intensity data;
data to obtain the desired radiate intensity of the x-ray tubes; and, selectively setting the high energy pulse width separately for each x-ray tube of the plurality of x-ray tubes.

* * * * *